(12) United States Patent
Toenges

(10) Patent No.: US 8,882,690 B2
(45) Date of Patent: Nov. 11, 2014

(54) ORTHOTIC DEVICE AND METHOD OF MANUFACTURE

(76) Inventor: Fred W. Toenges, Fort Wayne, IN (US)

( * ) Notice: Subject to any disclaimer, the term of this patent is extended or adjusted under 35 U.S.C. 154(b) by 531 days.

(21) Appl. No.: 12/927,482

(22) Filed: Nov. 16, 2010

(65) Prior Publication Data

US 2012/0123309 A1    May 17, 2012

(51) Int. Cl.
*A61F 5/00* (2006.01)
*A61F 5/01* (2006.01)

(52) U.S. Cl.
CPC ....... *A61F 5/0111* (2013.01); *A61F 2005/0172* (2013.01); *A61F 2005/0174* (2013.01)
USPC .................. 602/27; 602/30; 602/65; 128/882; 36/174; 36/180

(58) Field of Classification Search
USPC ......... 602/27–30, 65–66; 128/882; 36/89, 92, 36/93, 174–182
See application file for complete search history.

(56) References Cited

U.S. PATENT DOCUMENTS

| | | | |
|---|---|---|---|
| 4,446,856 A | 5/1984 | Jordan | |
| 4,672,955 A | 6/1987 | Cooper | |
| 4,776,326 A | 10/1988 | Young et al. | |
| 4,844,058 A | 7/1989 | Vogelbach | |
| 4,888,225 A | 12/1989 | Sandvig et al. | |
| 4,922,895 A * | 5/1990 | Chong | 602/29 |
| 5,174,052 A | 12/1992 | Schoenhaus et al. | |
| 5,231,723 A | 8/1993 | White et al. | |
| 5,323,549 A | 6/1994 | Segel et al. | |
| 5,370,604 A | 12/1994 | Bernardoni | |
| 5,573,501 A | 11/1996 | Ruscito et al. | |
| 5,593,383 A | 1/1997 | DeToro | |
| 5,797,862 A | 8/1998 | Lamont | |
| 5,810,754 A | 9/1998 | Kenosh | |
| 5,887,591 A | 3/1999 | Powell et al. | |
| 6,093,163 A * | 7/2000 | Chong et al. | 602/30 |
| 6,442,875 B1 * | 9/2002 | Joubert et al. | 36/115 |
| 6,517,505 B1 * | 2/2003 | Veldman | 602/27 |
| 7,455,651 B2 * | 11/2008 | Mollica | 602/65 |
| 2005/0240139 A1 * | 10/2005 | Bushby | 602/61 |
| 2007/0193071 A1 * | 8/2007 | Gilmore | 36/174 |
| 2012/0330207 A1 * | 12/2012 | Goswami et al. | 602/30 |

OTHER PUBLICATIONS

Nancy M. Hylton, R.P.T., Postural and Functional Impact of Dynamic AFOs and FOs in a Pediatric Population, JPO 1989; vol. 2, No. 1.

* cited by examiner

*Primary Examiner* — Nicholas Lucchesi
*Assistant Examiner* — Kari Petrik
(74) *Attorney, Agent, or Firm* — George Pappas

(57) ABSTRACT

An orthotic device having a thin, flexible material defining a plantar wall and lateral, medial and posterior sidewalls. A fastening mechanism releasably secures the lateral and medial sidewalls together. In some embodiments, the plantar wall defines a laterally extending distal trimline positioned distal of the first metatarsal head and proximal of the third, fourth and fifth metatarsal heads when the foot is secured within the orthotic device. In other embodiments, the device includes a heel post having a distal terminal edge with a medial portion extending into the arch proximal to the navicular bone and a lateral portion positioned proximal of the arch. In still other embodiments, an elongate strip of padding material projects inwardly below and proximate the medial malleosus and the lateral malleosus and is positioned to inhibit withdrawal of the calcaneous bone. A method of manufacturing an orthotic device is also disclosed.

19 Claims, 4 Drawing Sheets

ORTHOTIC DEVICE AND METHOD OF MANUFACTURE

BACKGROUND OF THE INVENTION

1. Field of the Invention

The present invention relates to orthotic devices adapted to be worn on a foot and, more particularly, to flexible orthotic devices which can be firmly secured about a foot and thereby enhance the stability of the ankle.

2. Description of the Related Art

Many individuals within the pediatric population suffer from pronation. Foot braces have often been employed in an effort to treat pronation by enhancing the stability of the ankle joint. More recently, dynamic ankle foot orthosis, often referred to as DAFOs, have been employed. Typically, DAFOs utilize a thin, flexible sheet of polymeric material that is vacuum formed onto a form. When the vacuum-formed sheet material is firmly secured about the foot of a patient, it increases the hydrostatic pressure within the foot and thereby enhances the stability of the joint.

DAFOs have provided several advantages over earlier rigid braces. DAFOs are generally tolerated more easily than rigid bracing because DAFOs are more flexible and allow some "give." As a result, the tendency of the patient to forceably "hold" against the brace is reduced. Because the DAFOs contact the foot over a large surface area, the pressure is distributed more evenly and skin breakdown problems are reduced.

While many advantages have already been obtained with existing DAFOs, further improvements are desirable.

SUMMARY OF THE INVENTION

The present invention provides an orthotic device which is firmly securable about a foot to thereby increase the hydrostatic pressure within the foot and enhance the stability of the ankle joint.

The invention comprises, in one form thereof, an orthotic device adapted to be worn on a foot having first, second, third, fourth and fifth metatarsal heads. The orthotic device includes a thin, flexible material defining a plantar wall, a lateral sidewall, a medial sidewall, and a posterior sidewall wherein each of the sidewalls extend upwardly from the plantar wall. A fastening mechanism releasably secures the lateral and medial sidewalls together to thereby firmly enclose the foot within the thin, flexible material. The plantar wall defines a laterally extending distal trimline positioned distal of the first metatarsal head and proximal of the third, fourth and fifth metatarsal heads when the foot is secured within the orthotic device.

The invention comprises, in another form thereof, an orthotic device adapted to be worn on a foot forming an arch of the foot and including a calcaneous bone, mid foot and metatarsal bones. The orthotic device includes a thin, flexible material defining a plantar wall, a lateral sidewall, a medial sidewall, and a posterior sidewall wherein each of the sidewalls extend upwardly from the plantar wall. The plantar wall defines an arch generally conforming to the arch of the foot. A fastening mechanism releasably secures the lateral and medial sidewalls together to thereby firmly enclose the foot within the thin, flexible material. A heel post is disposed on an exterior surface of the plantar wall and is positioned below and proximate the calcaneous bone. In some embodiments, the heel post has a distal terminal edge with a medial portion and a lateral portion wherein the medial portion of the distal terminal edge at least partially extends within the arch proximal to the navicular bone and the lateral portion of the distal terminal edge is positioned proximal of the arch.

The invention comprises, in still another form thereof, an orthotic device adapted to be worn on a foot having a medial malleolus and a lateral malleolus. The orthotic device includes a thin, flexible material defining a plantar wall, a lateral sidewall, a medial sidewall, and a posterior sidewall wherein each of the sidewalls extend upwardly from the plantar wall. A fastening mechanism releasably secures the lateral and medial sidewalls together to thereby firmly enclose the foot within the thin, flexible material. At least one elongate strip of resilient padding material projects inwardly from each of the medial and lateral sidewalls. The strip of material defines a downward facing surface and is disposed below and proximate the medial malleolus and the lateral malleolus and positioned to inhibit withdrawal of the calcaneous bone when the foot is secured within the orthotic device.

The invention comprises, in yet another optional embodiment thereof, a method of manufacturing an orthotic device adapted to be worn on a foot having a medial malleolus, a lateral malleolus, first, second, third, fourth and fifth metatarsal heads, forming an arch of the foot and including a navicular bone. The method includes providing a form having a configuration that is determined at least in part by physical properties of the foot; forming at least one groove in the form; and filling the groove with a first material. The method also includes forming a thin sheet of thermoformable polymer material over a substantial portion of the form including the groove filled with the first material to thereby join the thermoformable polymer material with the first material.

The invention comprises, in still another form thereof, a method of manufacturing an orthotic device adapted to be worn on a foot having a medial malleolus, a lateral malleolus, a calcaneous bone, first, second, third, fourth and fifth metatarsal heads, forming an arch of the foot and including a navicular bone. The method includes providing a form having a configuration that is determined at least in part by physical properties of the foot and forming a thin sheet of thermoformable polymer material over a substantial portion of the form wherein the thin sheet of thermoformable polymer material defines an orthotic device having a plantar wall, a lateral sidewall, a medial sidewall, and a posterior sidewall wherein each of said sidewalls extend upwardly from said plantar wall. The method also includes forming a distal trimline on the plantar wall that is positioned distal of the first metatarsal head and proximal of the third, fourth and fifth metatarsal heads when the foot is secured within the orthotic device.

The invention comprises, in yet another form thereof, a method of manufacturing an orthotic device adapted to be worn on a foot having a medial malleolus, a lateral malleolus, a calcaneous bone, first, second, third, fourth and fifth metatarsal heads, forming an arch of the foot, and including a navicular bone. The method includes providing a form having a configuration that is determined at least in part by physical properties of the foot and forming a thin sheet of thermoformable polymer material over a substantial portion of the form wherein the thin sheet of thermoformable polymer material defines an orthotic device having a plantar wall, a lateral sidewall, a medial sidewall, and a posterior sidewall wherein each of said sidewalls extend upwardly from said plantar wall and the plantar wall defines an arch generally conforming to the arch of the foot. The method also includes attaching a heel post to an exterior surface of the plantar wall.

BRIEF DESCRIPTION OF THE DRAWINGS

The above mentioned and other features of this invention, and the manner of attaining them, will become more apparent and the invention itself will be better understood by reference to the following description of an embodiment of the invention taken in conjunction with the accompanying drawings, wherein.

Figure 1:
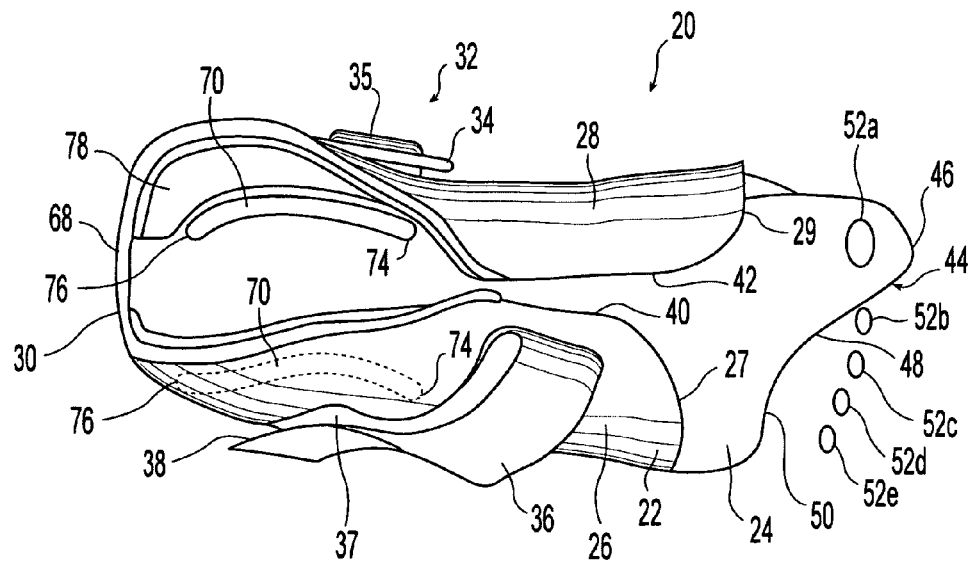
FIG. 1 is a top view of an orthotic device in accordance with the present invention.

Corresponding reference characters indicate corresponding parts throughout the several views. Although the exemplification set out herein illustrates an embodiment of the invention, in one form, the embodiment disclosed below is not intended to be exhaustive or to be construed as limiting the scope of the invention to the precise form disclosed.

DETAILED DESCRIPTION OF THE INVENTION

An orthotic device 20 in accordance with the present invention is shown in FIGS. 1-5. Orthotic device 20, also referred to herein as an orthosis, is formed by a thin sheet of flexible material 22. As discussed in greater detail below, flexible material 22 may be a sheet of polypropylene or other thermoplastic material that can be heated and vacuum formed or pulled over a form to thereby shape the flexible sheet material into the desired configuration. Although only a "right" orthosis 20 is illustrated and described below, a pair of orthosis 20 adapted for use with both feet will typically be provided to a patient.

After shaping into the desired configuration, the sheet material 22 forms a bottom plantar wall 24 that generally conforms to the bottom of the user's foot. Extending upwardly from plantar wall 24 are a lateral sidewall 26, a medial sidewall 28 and a posterior sidewall 30. A fastening mechanism 32 is used to secure the lateral and medial sidewalls 26, 28 together to thereby firmly enclose the foot within orthosis 20.

In the illustrated embodiment, fastening mechanism 32 includes a rigid ring 34 that is attached to medial sidewall 28 with a strap 35 that is attached with a rivet 33 or other suitable means, e.g., adhesives, to medial sidewall 28. Strap 35 and ring 34 are disposed at an approximately 45 degree angle to the plantar wall 24. A strap 36 for releasably engaging ring 34 is secured to lateral sidewall 26 with a rivet or in another suitable manner of securement, e.g., adhesives and is also disposed at an approximately 45 degree angle to the plantar wall. When securing orthosis 20 on a user's foot, strap 36 is threaded through ring 34, pulled snug and then folded back upon itself. Strap 36 includes a patch of hook 37 and loop 38 fasteners, e.g., Velcro® fasteners, so that strap 36 will be secured in place when it is folded back upon itself. The use of a releasable fastening mechanism 32 having a rigid ring 34 and securement strap 36 is well-known to those having ordinary skill in the art. Preferably, ring 34 is mounted on the medial sidewall 28 but the positions of ring 34 and strap 36 could be switched in alternative embodiments and/or alternative fastening mechanisms could be used to secure orthosis 20 on the foot of the user.

When securing fastening mechanism 32, the upper trimline 40 of lateral sidewall 26 and upper trimline 42 of medial sidewall 28 are pulled toward each other. In the illustrated embodiment, upper trimlines 40, 42 are positioned approximately parallel with each other on the dorsum or upper surface of the forefoot and leaving a small gap between upper trimlines 40, 42 when orthosis 20 is secured on a foot.

Figure 3:
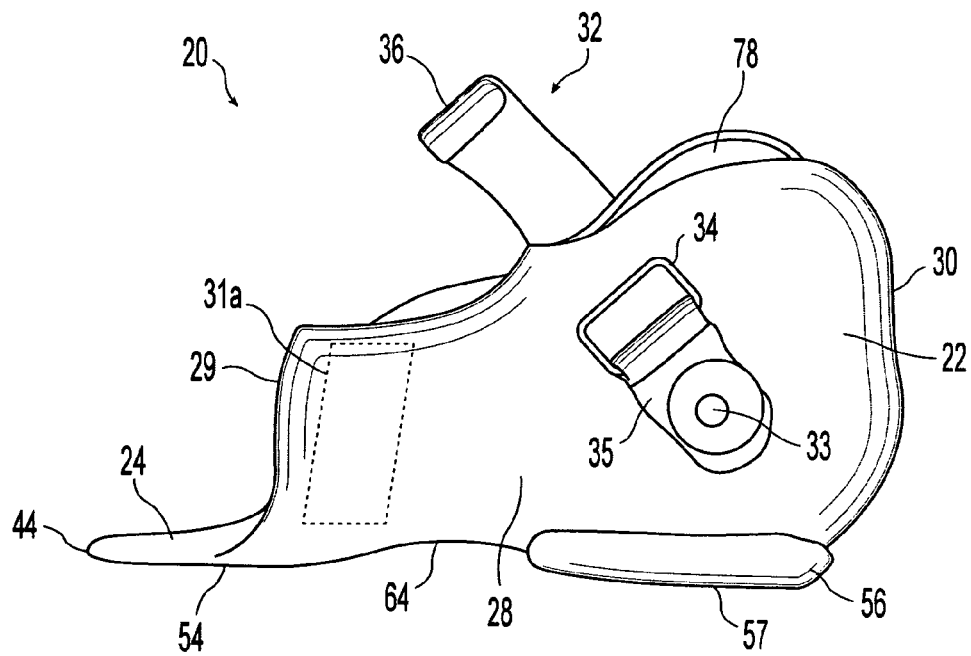
FIG. 3 is a side view of the orthotic device.
Figure 4:
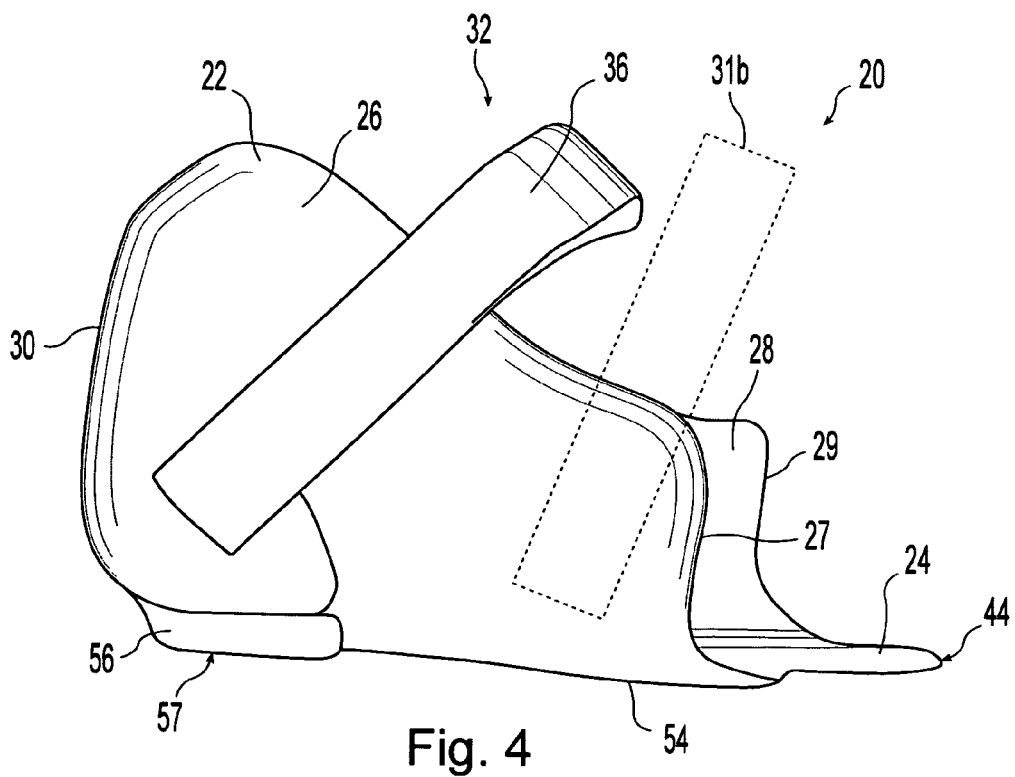
FIG. 4 is another side view of the orthotic device.

An optional second fastening mechanism located distal of mechanism 32 may also be employed with orthosis 20. As can be seen in FIGS. 3 and 4, the second fastening mechanism may take the form of a strip 31a of hook or loop fasteners adhered to sidewall 28. A strap 31b having a patch of cooperating hook or loop fasteners located thereon is secured to the opposite sidewall 26 and can be brought into contact with strip 31a to secure sidewalls 26, 28 together.

As most easily seen in FIG. 1, plantar wall 24 defines a laterally extending distal trimline 44. Plantar wall 54 also defines an arch 64 that generally conforms to the arch of the foot 66 of the user. The arch of the user's foot is a well-known anatomical feature that is collectively formed by the medial long, tunal, metatarsal, tarsus and cuboid arches of the user. The outline of arch 64 is shown by a dashed line in FIG. 2.

Distal trimline 44 includes a medial section 46, a transitional section 48 and a lateral section 50. FIG. 1 schematically depicts the approximate location of the first through fifth metatarsal heads 52a-52e of the user's foot. As can be seen in FIG. 1, medial section 46 of trimline 44 is located distal of the first metatarsal head 52a. Lateral section 50 of trimline 44 is located proximal of the third, fourth and fifth metatarsal heads 52c, 52d and 52e. In the illustrated embodiment, lateral section 50 is also located distal to arch 64. Transition section 48 of distal trimline 44 connects the medial and lateral sections 46, 50. Transition section 48 of trimline 44 is located near the second metatarsal head 52b and may be located either distal or proximal of the second metatarsal head 52b.

The use of a plantar wall 24 having a distal trimline 44 as shown in FIG. 1 is believed to provide significant benefits to the user. More specifically, a plantar wall 24 having a distal trimline 44 which is located distal of the first metatarsal head 52a and proximal of the third through fifth metatarsal heads 52c-52e provides support to the first metatarsal head is thereby believed to help control pronation without encouraging toe-out.

Figure 2:
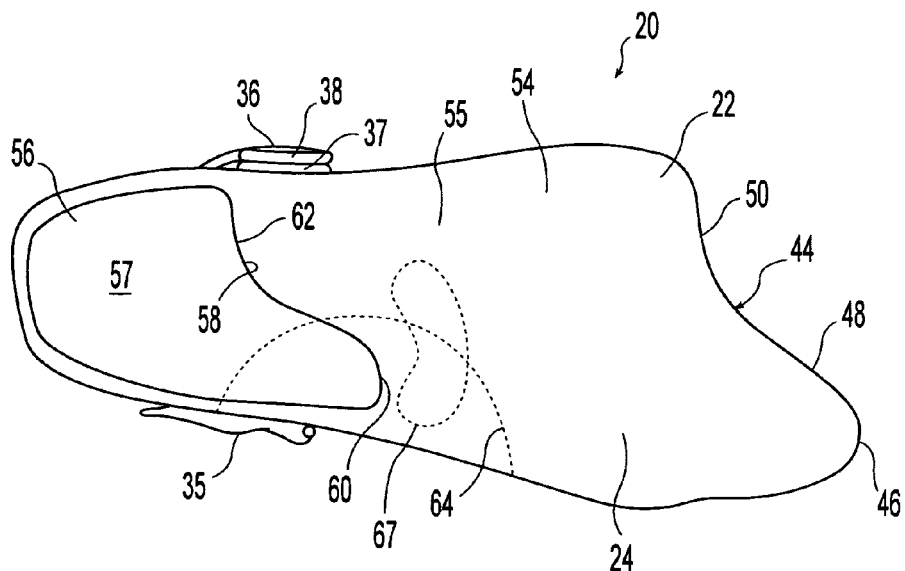
FIG. 2 is a bottom view of the orthotic device.

As can be seen in FIG. 2, a heel post is secured to the bottom or exterior surface 54 of plantar wall 24. Heel post 56 includes a distal terminal edge 58 having a medial portion 60 and a lateral portion 62. The medial portion 60 of terminal edge 58 extends into arch 64 to a location near and proximal to the position of the user's navicular bone 67. Lateral portion 62 of the terminal edge 58 of heel post 56 is positioned proximal of arch 64. The use of a heel post 56 having an extended medial portion 60 is believed to help control pronation from mid-step through heel off.

As best seen in FIGS. 3 and 4, the bottom surface 57 of heel post 56 is substantially coplanar with the non-arch portion 55 of exterior surface 54 of plantar wall 24 when plantar wall is unflexed. In other words, heel post 56 does not elevate the heel of the user.

Medial sidewall 28 is shown in FIG. 3 and has a distal vertically extending edge 29. In the illustrated embodiment, the distal vertically extending edge 29 of medial sidewall 28 is located proximal to the first metatarsal head and medial section 46 of distal trimline 44.

Lateral sidewall 26 is shown in FIG. 4. In the illustrated embodiment, the distal vertically extending edge 27 is located proximal to the fifth metatarsal head and lateral section 50 of distal trimline 44.

Figure 5:
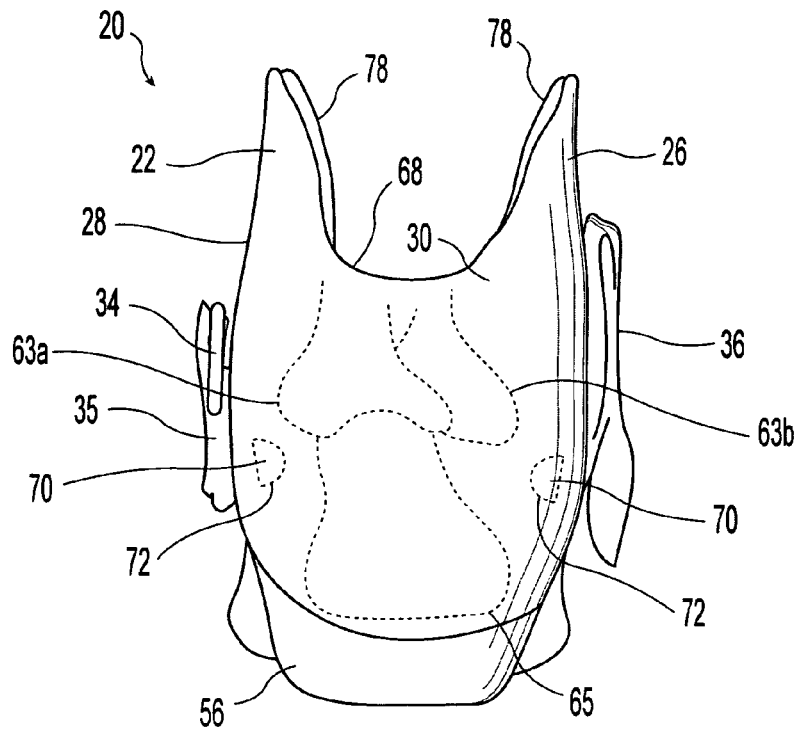
FIG. 5 is a rear view of the orthotic device.
Figures 6, 7:
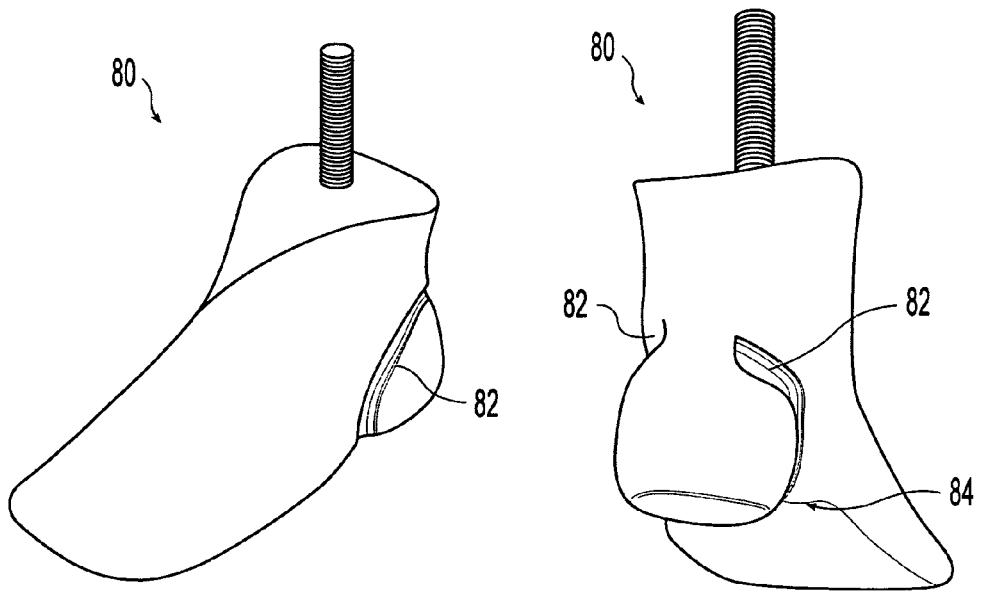
FIG. 6 is a front perspective view of a form used in the manufacture of an orthotic device.
FIG. 7 is a rear perspective view of the manufacturing form.
Figure 8:
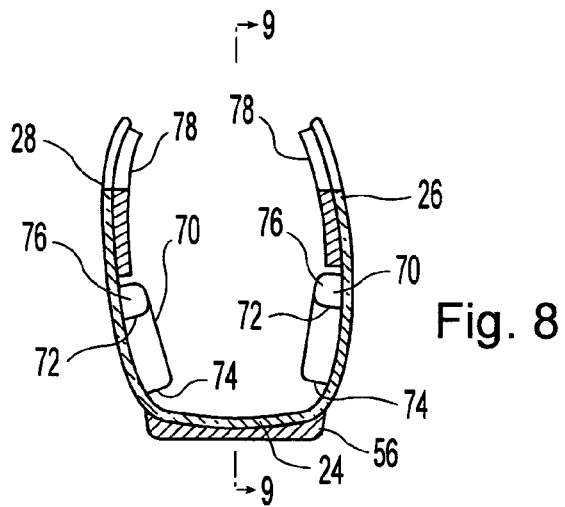
FIG. 8 is a cross sectional view taken along line 8-8 of FIG. 9.

Turning now to FIG. 5, posterior sidewall 30 is best seen. Posterior sidewall 30 has a generally U-shaped upper trimline 68. U-shaped trimline 68 has a lower portion near the site of the Achilles tendon insertion to the calcaneous bone and extends upwardly proximal to both the lateral and medial malleolus. By positioning posterior trimline 68 just above the level of the ankle fulcrum of movement, complete coverage of the calcaneous bone can be obtained while still permitting comfortable ankle movement.

Orthosis 20 may optionally include a pair of elongate strips of resilient padding material 70. Padding strips 70 project inwardly from sidewalls 26, 28 and are made of a soft resilient material such as a closed cell foam. Padding strips 70 are positioned to help control medial lateral motion of the calcaneous bone and inhibit pronation.

Figure 9:
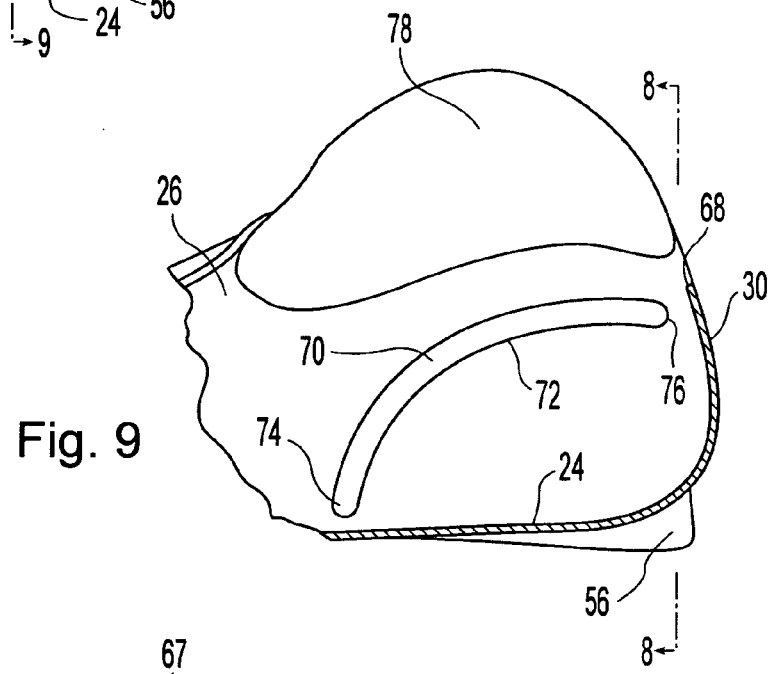
FIG. 9 is a cross sectional view taken along line 9-9 of FIG. 8.
Figure 10:
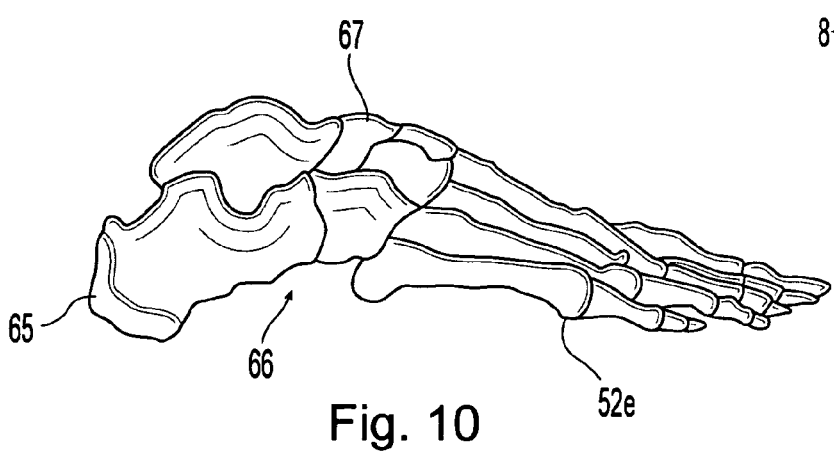
FIG. 10 is a side view of the bones of a human foot.

The configuration of padding strips 70 is best understood with reference to FIG. 9. FIG. 5 schematically depicts the relationship of strips 70 relative to the calcaneous bone 65, the medial malleolus 63*a* and the lateral malleolus 63*b* at the upper portion of padding strips 70 near upper end 76 of padding strip 70. The calcaneous bone is colloquially known as the heel bone while the lateral and medial malleolus are colloquially known as the ankle bones.

Padding strips 70 generally follow the calcaneal groove formed between the medial and lateral malleolus and the lower projecting portions of the calcaneous bone on the medial and lateral sides of the foot. In colloquial terms, strips follow the grooves located between the heel and ankle bones on the opposite sides of the foot. Positioning padding strips 70 in this manner places them on the medial and lateral sidewalls 28, 26 below and proximate the medial malleolus 63*a* and lateral malleolus 63*b* and positioned to inhibit withdrawal of the calcaneous bone 65 when the user's foot is secured within orthosis 20.

More specifically, padding strip 70 located on medial sidewall 28 extends in an arcuate path from a first end 74 proximate plantar wall 24 and just proximal arch 64 and curves in a generally circular path through an approximately 90 degree angle to a second end 76 located where medial sidewall 28 transitions to the posterior sidewall 30. At second end 76, padding strip 70 is at a height that is approximately the same as the lower limit of the U-shaped posterior trimline 68 which corresponds to the insertion location of the Achilles tendon to the calcaneous bone 65. In other words, padding strip 70 forms a generally circular arc from a first end 74 located proximate plantar wall 24 to a second end 76 located proximate posterior sidewall 30. The strip of padding material 70 located on the opposite lateral sidewall 26 forms a mirror image of padding strip 70 on medial sidewall 28.

Padding strips 70 project inwardly and thereby define a downward facing surface 72. Surface 72 inhibits the withdrawal of the user's calcaneous bone 65 when orthosis is secured on the user's foot.

A layer of padding 78 is located opposite the medial and lateral malleolus above the inwardly projecting elongate strip of material. Padding 78 may take the form of a closed cell polyethylene foam. The lower edge of padding 78 is located near the upper edge of padding strips 70 proximate posterior sidewall 30 and at approximately the same level as the bottom of the U-shaped posterior trimline 68 as padding 78 extends distally. Padding 78 extends upwardly to upper trimlines 40, 42. The extent of padding 78 is best understood with reference to FIG. 9.

Padding 78 provides a cushion between sidewalls 26, 28 and the lateral and medial malleolus 63*b*, 63*a*. In the illustrated embodiment, padding strips 70 are thicker than padding 78 and project further inwardly than padding 78. Padding 78 enhances the comfort of orthosis 20 when the foot is stationary and when it is in motion.

Movement of the ankle and most of the other important joints of the foot involve movement components in three planes of movement. In such triplane joints, movements in the different planes are interconnected. If movement is restricted or stabilized in one or two planes, the movement in the remaining plane will be graded and stable.

Because orthosis 20 is a volume based orthosis, much like a prosthetic socket, the increase in fluid pressure within the foot, i.e., hydrostatic pressure, when orthosis 20 is secured on the foot, enhances the stability of the foot. Orthosis 20 allows small increments of movement within the foot to occur. Small increments of movement about the midline typically occur in both weightbearing and non-weightbearing situations as a part of normal balance strategies. Extremes of movement or fixation are normal and do not provide normal proprioceptive feedback information to the postural control mechanism within the central nervous system. By resisting extreme movements and permitting small increments of movement, orthosis 20 enhances stability and provides helpful proprioceptive feedback to the central nervous system to thereby enhance balance and postural control.

Orthosis 20 is a low tone supramalleor orthosis and provides support to the foot while allowing natural movement during the gait cycle. The unique distal trimline 44 of the plantar wall 24 supports the forefoot while allowing metatarsal flexing. Use of a plantar wall 24 having a distal trimline 44 with medial section 46 positioned distal of the first metatarsal head and a lateral section 50 positioned proximal of the third, fourth and fifth metatarsal heads helps to control both pronation and excessive toeing out. The elongate projecting padding strips 70 gently grasp the calcaneous bone and is also thought to inhibit excessive pronation. Heel post 56 with its extended medial anatomical section defining a medial portion 60 that extends into arch 64 is also believed to control pronation from mid-step through heel off. As a result, the illustrated orthosis 20 allows for substantially natural motion of the foot ankle complex while fostering proper alignment when the patient is standing, walking or running.

The manufacture of orthosis 20 will now be discussed. A custom mold of the foot of the patient is taken and measurements of the foot are taken. More specifically, the following measurements are taken: 1) length of foot; 2) length from heel to just distal of first metatarsal head; 3) length from heel to just proximal of fifth metatarsal head; 4) width of foot across first to fifth metatarsal heads; 5) outer width of leg from medial malleolus to lateral malleolus; 6) width of foot at heel; 7) circumference of foot at cuboid arch (instep); and 8) circumference of proximal ankle.

A model or manufacturing form 80 corresponding to the foot is then made. The form 80 generally conforms to the foot of the patient but varies in some respects. More specifically, form 80 is modified so that it represents a neutral biomechanical foot and the cuboid arch 84 on form 80 is enlarged. If the use of padding strips 70 is desired, grooves 82 can placed in manufacturing form 80 at the location of strips 70.

After completion of manufacturing form 80, grooves 82 are filled with a first material that will form padding strips 70. In the illustrated embodiment, the material used to fill grooves 82 forms a closed cell polypropylene foam. After filling grooves 82, a thin sheet of thermoformable material such as a 3/32 inch thick polypropylene or a co-polymer sheet is vacuum formed over manufacturing form 80 and stretched to an almost paper thin thickness across the anterior portion above the dorsum. Padding 78 is then adhered to the interior of sidewalls 26, 28 and the fastening mechanisms are attached.

Alternatively, padding strips 70 can be adhered or otherwise attached to the interior surface of the thermoformable material after it has been shaped instead of employing grooves 82.

While this invention has been described as having an exemplary design, the present invention may be further modified within the spirit and scope of this disclosure. This application is therefore intended to cover any variations, uses, or adaptations of the invention using its general principles.

What is claimed is:

1. An orthotic device adapted to be worn on a foot having an ankle joint and first, second, third, fourth and fifth metatarsal heads for increasing hydrostatic pressure within the foot and enhancing stability of the ankle joint and for controlling pronation, said orthotic device comprising:
    a sheet of material shaped into a configuration defining a plantar wall, a lateral sidewall, a medial sidewall, and a posterior sidewall wherein each of said sidewalls extend upwardly from said plantar wall;
    a fastening mechanism releasably securing said lateral and medial sidewalls together to thereby firmly enclose the foot within said configuration; and
    wherein the plantar wall defines a laterally extending distal trimline including a medial section, a transitional section and a lateral section, wherein said transition section connects said medial section and said lateral section and wherein, when the foot is secured within said orthotic device, said medial section of said distal trimline is located distal of the first metatarsal head and said lateral section of said trimline is located proximal of the third, fourth and fifth metatarsal heads;
    wherein said medial sidewall extends from said posterior sidewall to a distal vertically extending edge located proximal said medial section of said distal trimline; and,
    wherein said lateral sidewall extends from said posterior sidewall to a distal vertically extending edge located proximal said lateral section of said distal trimline.

2. The orthotic device of claim 1 further comprising a heel post disposed on an exterior surface of said plantar wall, said heel post having a distal terminal edge with a medial portion and a lateral portion wherein said medial portion is positioned distal of said lateral portion.

3. The orthotic device of claim 2 wherein said plantar wall defines an arch adapted to generally conform to an arch of the foot and said medial portion of said distal terminal edge at least partially extends within said arch proximal to a navicular bone of the foot and said lateral portion of said distal terminal edge is positioned proximal of said arch.

4. The orthotic device of claim 1 wherein said orthotic device further comprises a resilient padding material projecting inwardly from each of said medial and lateral sidewalls wherein said padding material is adapted to be disposed below and proximate a medial malleolus and the lateral malleolus of the foot and positioned to inhibit withdrawal of the calcaneous bone of the foot when the foot is secured within said orthotic device.

5. The orthotic device of claim 1 wherein said posterior sidewall defines a substantially U-shaped trimline and said fastening mechanism includes a D-ring secured to one of said lateral and medial sidewalls and a strap secured to the other of said lateral and medial sidewalls, said strap being releasably securable to said D-ring.

6. The orthotic device of claim 1 wherein said sheet of material comprises a thermoformable material which is heated and shaped into said configuration.

7. The orthotic device of claim 6 wherein said thermoformable sheet material is about $3/32$ inch thick.

8. The orthotic device of claim 7 wherein said thermoformable sheet material comprises one or more of a polypropylene and co-polymer materials.

9. The orthotic device of claim 1 wherein said posterior sidewall defines a substantially U-shaped upper trimline.

10. An orthotic device adapted to be worn on a foot having an ankle joint and first, second, third, fourth and fifth metatarsal heads for increasing hydrostatic pressure within the foot and enhancing stability of the ankle joint and for controlling pronation, said orthotic device comprising:
    a sheet of material shaped into a configuration defining a plantar wall, a lateral sidewall, a medial sidewall, and a posterior sidewall wherein each of said sidewalls extend upwardly from said plantar wall;
    a fastening mechanism releasably securing said lateral and medial sidewalls together to thereby firmly enclose the foot within said configuration; and
    wherein the plantar wall defines a distal trimline comprising a medial section adapted to be positioned distal of the first metatarsal head and a lateral section adapted to be positioned proximal of the third, fourth and fifth metatarsal heads when the foot is secured within said orthotic device;
    wherein said medial sidewall extends from said posterior sidewall to a distal vertically extending edge located proximal said medial section of said distal trimline; and,
    wherein said lateral sidewall extends from said posterior sidewall to a distal vertically extending edge located proximal said lateral section of said distal trimline.

11. The orthotic device of claim 10 wherein said distal trimline edge further comprises a transition section connecting said medial and lateral sections, said transition section adapted to be located near the second metatarsal head.

12. The orthotic device of claim 11 wherein said sheet of material comprises a thermoformable material which is heated and shaped into said configuration.

13. The orthotic device of claim 12 wherein said thermoformable sheet material is about $3/32$ inch thick.

14. The orthotic device of claim 13 wherein said thermoformable sheet material comprises one or more of a polypropylene and co-polymer materials.

15. The orthotic device of claim 10 further comprising a heel post disposed on an exterior surface of said plantar wall, said heel post having a distal terminal edge with a medial portion and a lateral portion wherein said medial portion is positioned distal of said lateral portion.

16. The orthotic device of claim 15 wherein said plantar wall defines an arch adapted to generally conform to an arch of the foot and said medial portion of said distal terminal edge at least partially extends within said arch proximal to a navicular bone of the foot and said lateral portion of said distal terminal edge is positioned proximal of said arch.

17. The orthotic device of claim 10 wherein said orthotic device further comprises a resilient padding material projecting inwardly from each of said medial and lateral sidewalls wherein said padding material is adapted to be disposed below and proximate a medial malleolus and the lateral malleolus of the foot and positioned to inhibit withdrawal of the calcaneous bone of the foot when the foot is secured within said orthotic device.

18. The orthotic device of claim 10 wherein said posterior sidewall defines a substantially U-shaped trimline and said fastening mechanism includes a D-ring secured to one of said lateral and medial sidewalls and a strap secured to the other of said lateral and medial sidewalls, said strap being releasably securable to said D-ring.

19. The orthotic device of claim 10 wherein said posterior sidewall defines a substantially U-shaped upper trimline.

* * * * *